United States Patent
Keong

(10) Patent No.: US 7,435,428 B2
(45) Date of Patent: Oct. 14, 2008

(54) METHOD OF MANUFACTURING A HAND HEALTH CARE GLOVE

(75) Inventor: Wong See Keong, Darul Khusus (MY)

(73) Assignee: NS Uni-Gloves SDN BHD, Seremban (MY)

( * ) Notice: Subject to any disclaimer, the term of this patent is extended or adjusted under 35 U.S.C. 154(b) by 483 days.

(21) Appl. No.: 11/065,706

(22) Filed: Feb. 23, 2005

(65) Prior Publication Data

US 2006/0188552 A1 Aug. 24, 2006

(51) Int. Cl.
*A61K 9/00* (2006.01)
*A61F 13/10* (2006.01)

(52) U.S. Cl. ...................................... 424/443; 424/400

(58) Field of Classification Search .................. None
See application file for complete search history.

(56) References Cited

U.S. PATENT DOCUMENTS

| | | | | |
|---|---|---|---|---|
| 4,070,451 | A | 1/1978 | Price | 424/61 |
| 5,208,013 | A | 5/1993 | Klein | 424/59 |
| 5,560,904 | A * | 10/1996 | Laugier et al. | 424/78.08 |
| 6,274,154 | B1 * | 8/2001 | Chou | 424/402 |
| 2004/0115250 | A1 * | 6/2004 | Loo et al. | 424/443 |

\* cited by examiner

*Primary Examiner*—M P Woodward
*Assistant Examiner*—Melissa S Mercier
(74) *Attorney, Agent, or Firm*—IPLA P.A.; James E. Bame

(57) ABSTRACT

A process for creating a disposable glove which has been specially treated with a uniform coating of the Lanolin and Vitamin-E composite through a specially controlled application and drying process. The process satisfies the need to minimize the side effects of skin damage and irritation due to prolonged and extensive application of hand gloves in the health care industry.

14 Claims, 3 Drawing Sheets

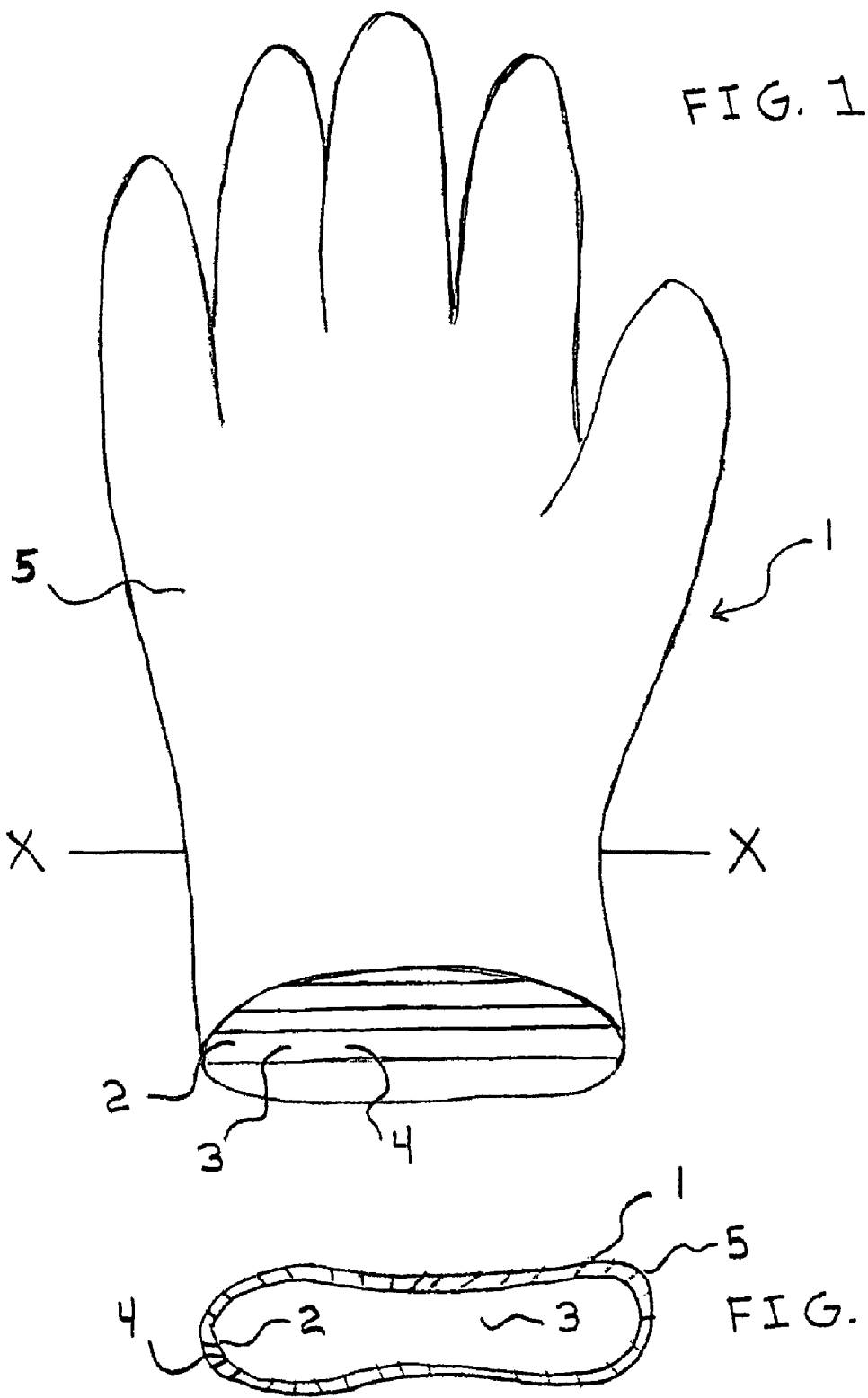

LANO-E POWDER FREE TREATMENT PROCESS FLOW CHART

GLOVES MANUFACTURING PROCESS FLOW OUTLINE

| 1 | Stripping Area | 9 | Drying Oven | 17 | Post Leaching Tanks |
| --- | --- | --- | --- | --- | --- |
| 2 | Powder Wash Tank | 10 | Dipping Tank | 18 | Chalk Tank |
| 3 | Acid Tank | 11 | Gelling Oven | | |
| 4 | Rinsing Tank 1 | 12 | Leaching 1 | | |
| 5 | Rinsing Tank 2 | 13 | Leaching 2 | | |
| 6 | Rinsing Tank 3 | 14 | Polymer Tank | | |
| 7 | Rinsing Tank 4 | 15 | Beading | | |
| 8 | Coagulant Tank | 16 | Top Oven | | |

METHOD OF MANUFACTURING A HAND HEALTH CARE GLOVE

FIELD OF INVENTION

This invention relates specifically to the needs of incorporating hand health-care features and benefits into gloves by forming a coating of purified Lanolin and Vitamin E onto the donning surface of disposable gloves to soothe the hands during and after a prolonged and routine application of disposable gloves.

BACKGROUND

With the increased demands and awareness from the general public for healthcare professionals to be accountable for their actions, good infection control is crucial in nursing practices. To achieve higher standards of clinical practice, safe practices to minimize the risk of cross-infection have become the uppermost in the minds of healthcare professionals when caring for patients. Disposable gloves are commonly used as a protective device for the purpose. In the process of escalating dependence for such essential protective device in today's modern health-care industry, thirty-five percent of healthcare workers who wear medical gloves may experience non-allergic skin problems at one time or another (9). The most frequently experienced is irritant contact dermatitis. The characteristics of this non-immune reaction consist of dry, crusty, hard bumps along with horizontal skin cracks. Frequent hand washing, strong surgical scrubbing agents, soaps, detergents, glove powders and the hot moist environment caused by glove wear are all associated with irritant contact dermatitis. Every time we wash our hands we remove the natural oils that are essential for healthy skin. When there is a deficiency of natural oils, the skin tends to dry and loses its resilience and eventually cracks. This skin reaction may be minimized by avoiding as much as possible all of the causative factors in the workplace and home environment. In this case, the use of an emollient like lanolin has been found helpful.

The history of lanolin is both long and fascinating (1,2,3). Lanolin was known to and used by the ancient Greeks as an excellent emollient. Its strength as an active ingredient in skincare application lies in its extensive records of safe use for the purpose. Lanolin is a mixture of esters derived from several fatty acids. With water it readily forms an emulsion. The literatures on skin surface studies have provided objective evidence and confirmed the emollient effect of lanolin and its derivatives (4,5,10). In addition to this, lanolin has demonstrated remarkable chemical and physical similarities in comparison to human skin lipids (6). Its presence will help to condition the skin of the user's hands.

The invention to apply Lanolin onto gloves is further enriched by the addition of Vitamin E into the formulation. Vitamin E is a powerful biological antioxidant (7,8) that serves to prevent disease and premature aging. It has a neutralizing effect on free radicals, a by-product of energy metabolism. Vitamin E is an important antioxidant commonly known for its ability to aid in the healing of previously damaged skin. It also tends to improve skin elasticity and thus promotes a youthful and healthy look to the skin.

The application of the moisturizing and therapeutic ingredients made of emulsified Lanolin and Vitamin E (known as Lano-E composite herein) to the gloves will substantially provide additional hand health care features, in addition to, its basic function as a barrier to control cross contamination, especially in the medical and laboratory procedures.

BACKGROUND REFERENCES

1. Clark, E. W.; A brief history of lanolin, Pharm. Hist., 10, 5-6 (1980)
2. Orr, S. R.; From Oesypus to Medilan—a short account of the history of lanolin, SCS Newsletter, 7-8, Oct. (1996).
3. Orr, S. R.; A brief guide to lanolin technology and applications, Lipid Technology, 10 (No. 1), 10-14, (1998).
4. Orr, S. R.; The activity of a natural emollient: lanolin, pp 83-96 of the Proceedings of the Active Ingredients Conference, Paris, 13-14 Nov. (1996).
5 Orr, S. R. and Steel, I.; Lanolin emolliency: fact or fiction?. Poster presented at the 4th. Congress of the European Academy of Dermatology and Venereology, Brussels, 10-14 Oct. (1995).
6 Dr. Steve Orr, Argonaut Works, Laisterdyke, Bradford BD4 8AU, United Kingdom, Lanolin Demythologised (1998)
7. Traber MG. Vitamin E. In: Shils ME, Olson JA Shike M, Ross Ac, ed. Modern Nutrition in Health and Disease. $10^{th}$ ed. Baltimore: Williams & Wilkins, 1999: 347-62
8. Farrell P and Robert R. Vitamin E. In: Shils MK, Olson JA, and Shike M, ed. Modern Nutrition in Health and disease. $8^{th}$ ed. Philadelphia, Pa.: Lea and Febiger 1994: 326-41
9. David Tilton, Latex—Itching to know more—Nurse CEUs, Wild iris Medical Education 2003: 2-3
10. J. Thewlis, The emollience of Lanolin, Croda Chemical Ltd 1991: 7

SUMMARY OF THE INVENTION

The invention satisfies the need to minimize the side effects of skin damage and irritation due to prolonged and extensive application of the gloves. This invention herein describes a new disposable glove that has been specially treated with a uniform coating of the Lano-E composite through a specially controlled drying process and a method for manufacturing such hand health care glove. The glove can be made of natural rubber latex or synthetic materials, such as, acrylonitrile, polyurethane, polychloroprene and polyvinyl chloride. The glove that is manufactured in this manner has the following attributes during use:

a) The multiple cycles of washing and rinsing processes by chlorination remove the powder residue, kill microorganisms and remove water soluble impurities including allergenic proteins. The powder residue exists in the form of cornstarch for donning purposes that is applied in stage 18 (referring to FIG. 4) of the process and calcium carbonate as a mold release agent that is applied in stage 8 of the process. There are also powder residues of accelerators, sulphur, zinc oxide and antioxidants, which are vulcanizing chemicals and preservatives that area applied in stage 10 of the process.

b) The glove possesses a coating of Lano-E composite on the donning surface that can help the hands to maintain skin elasticity and to heal previously damaged skin.

c) The Lano-E composite is formulated in such a way that the composition is adequate to provide a well balanced, non greasy optimum smoothness without affecting the durability and flexibility of the bulk materials of the glove.

d) The dried Lanolin and Vitamin E becomes emulsified and are released from the interior surface of the glove upon being dampened by sweat during use. The emulsified mixture is then released onto the user's hands, which helps to condition and moisturize the skin.

A method of manufacturing a hand health care disposable glove includes the following steps. Initially a disposable glove is formed from natural rubber latex or other synthetic materials like acrylonitrile, polyurethane, polychloroprene or polyvinyl chloride through a dipping process. The normal orientation of the glove has an interior with a donning surface and an exterior surface. An initial step is inverting the glove inside out, so the donning surface is exposed. Then, subjecting the glove through a series of controlled chlorination washing processes. Coating the donning surface of the glove with a coating of an emulsified mixture of Lanolin and Vitamin E using water as a liquid medium. Evaporating the liquid medium from the emulsified mixture in a temperature controlled heating condition to achieve a dried coating of purified lanolin enriched with Vitamin E formed on the donning surface of the glove.

Although the present invention is briefly summarized, a fuller understanding of the invention can be obtained from the following drawings, detailed description and appended claims.

BRIEF DESCRIPTION OF THE DRAWINGS

These and other features, aspects and advantages of the present invention will become better understood with reference to the accompanying drawings, wherein:

FIG. 1 Shows a front view of the glove, depicting the exterior surface and the donning surface of the interior portion.

FIG. 2 Shows a cutaway view of the glove along the x-x line of FIG. 1.

DETAILED DESCRIPTION OF THE INVENTION

Figure 3:
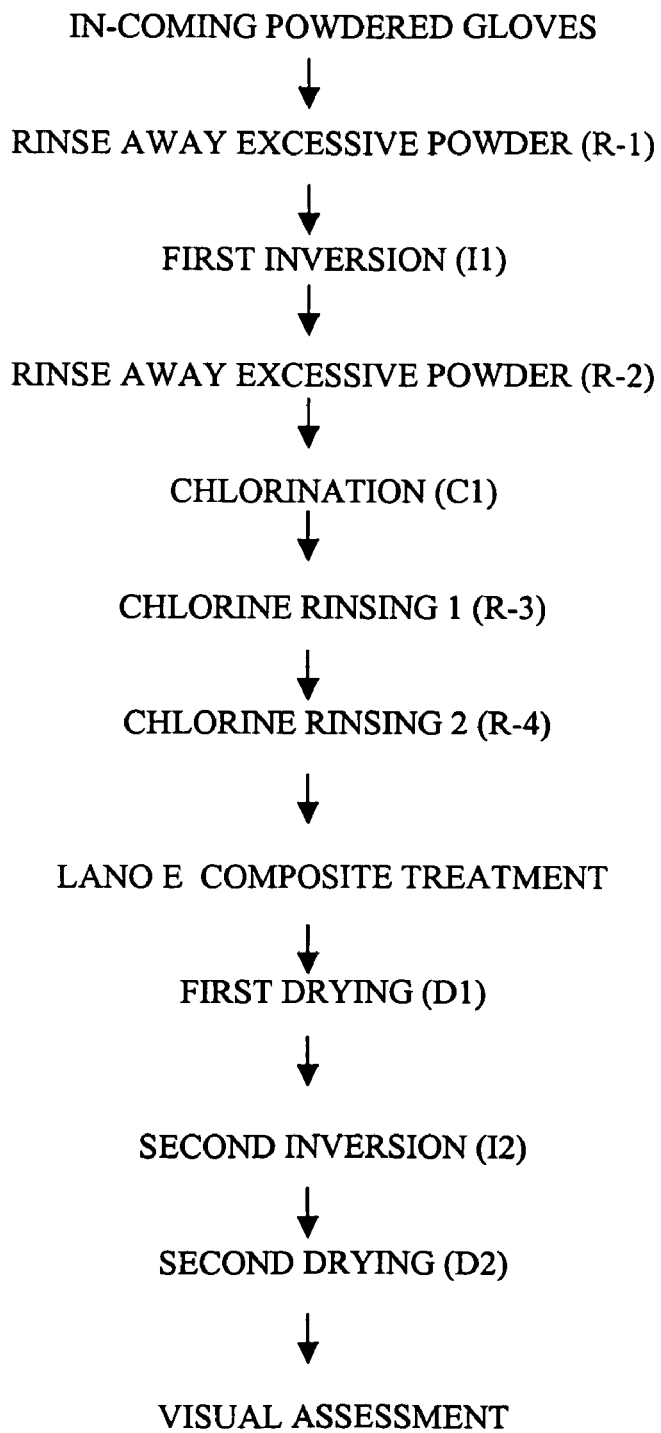
FIG. 3 Illustrates the flow chart for the application of the Lano-E coating.
Figure 4:
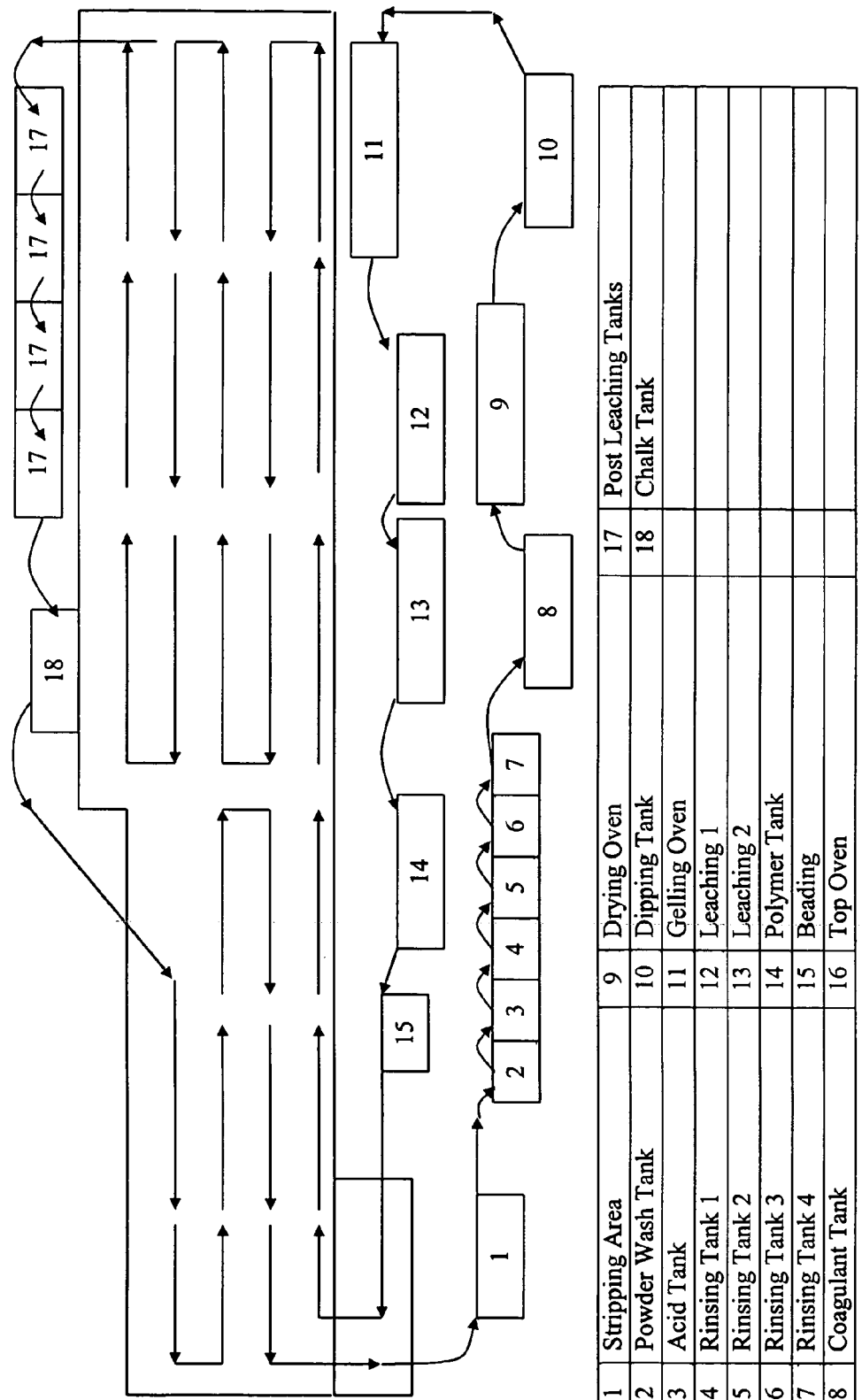
FIG. 4 Illustrates the gloves manufacturing process flow outline, which is the production of the gloves prior to the process of applying the Lano-E coating.

Referring to FIGS. 1 and 2, the present invention is a process for manufacturing a thin-walled disposable glove 1 as shown in FIG. 1, which has been manufactured in such a way that the donning surface 4 is uniformly coated with a layer of dehydrated Lano-E composite 2. The Lano-E composite 2 is comprised of a coating of Lanolin and Vitamin E that is adequate to provide a well balanced, non-greasy optimum smoothness without affecting the durability and flexibility of the bulk materials that make the glove 1. The glove 1 can be made of natural rubber latex or synthetic materials such as acrylonitrile, polyurethane and polychloroprene. In one preferred embodiment, the material is natural rubber latex. FIG. 3 details the steps in the special process for applying the Lano-E composite 2 coating. The glove 1 has an interior 3 with a donning surface 4 and an exterior surface 5. The gloves 1 are initially manufactured by a dipping process, which is a well known method of manufacturing within the industry. FIG. 4, "Gloves Manufacturing Process Flow Outline" briefly details the basic steps in such a dipping process. Once the glove manufacturing process is complete the process for application of mixture of Lanolin and Vitamin E is begun.

The mixture of Lanolin and Vitamin E or rather Lano-E composite 2 is formulated in such a way that the composition is optimized and adequate to provide a well balanced, non greasy optimum smoothness without affecting the durability and flexibility of the bulk materials of glove. The Lano-E composite 2 is evenly applied onto the donning surface 4 of glove. In one preferred embodiment the thickness of the dehydrated coat of Lano-E composite 2 is about 0.01 mm. A range of about 0.005 mm to about 0.02 mm coating of Lano-E 2 has been found to provide a well balanced, non-greasy optimum smoothness without affecting the durability and flexibility.

The application of the mixture of Lanolin and Vitamin E to the glove involves treating the glove 1 by a series of washing processes that remove the powder, water-soluble impurities and microbes. The incoming powdered glove 1 is first water rinsed (R-1) to remove excess powder from the exterior surface of the glove. A glove 1 in its normal orientation is then inverted (I1) inside-out so that the donning surface 4 becomes the outside external portion of the glove and the normally exterior surface 5 is temporarily the internal portion of the glove. The gloves 1 are again rinsed (R-2) with water to remove excess powder from primarily the donning surface 4 of the glove. The glove 1 is exposed to series of controlled chlorination washing processes.

The glove 1 is exposed to chlorine gas (C1) in an enclosed chamber using water as the aqueous medium to facilitate the reaction to take place. The intensity of chlorination is carefully controlled to optimize the degree of treatment on both the donning surface 4 and the exterior surface 5 of the glove without overly exposing the surfaces to the chlorine gas. The chlorine gas is produced from reactions between Sodium Hypochlorite and Hydrochloric acid. The chlorine is at a concentration of about 850 ppm in water, with a range of between about 700 ppm and 1000 ppm being satisfactory. Over exposure to the chlorine gas can be very damaging to the physical properties of the finished product.

Following the chlorination washing process the glove 1 is water rinsed two more time in rinse (R-3) and rinse (R-4) to remove the chlorine residue. On completion of the chlorine gas washing and the water rinsing cycles (R-3 and R-4), the glove is then treated with Lano-E composite 2 before heating (D1 and D2) the glove 1 to complete dryness. A visual assessment is performed upon completion of the drying process.

Lano-E composite 2 is first prepared in a bulk quantity of concentration comprising by weight of 5 parts of Pure Lanolin tablets and 15 parts of Vitamin E in the form of alpha-tocopheryl acetate. The mixture is blended homogeneously with 80 parts by weight warm water at 45 degree Celsius to form an emulsified mixture. The water temperature can vary from between about 35 degree Celsius to about 55 degree Celsius. To apply the composite 2 onto the donning surface 4, the gloves 1 can be soaked and/or agitated in a bath of the emulsified mixture for about 5 minutes in an enclosed rotating drum. Alternatively, the emulsified mixture can be sprayed onto the surfaces of the glove 1. The former method is preferred because the application of the mixture onto the glove will be complete and uniform. A pre-defined quantity shall be determined and followed for the treatment. Typically, about 900 liters of emulsified mixture is blended in a 2000 liter rotating drum, although the amount may vary.

About 15,000 glove pieces can be coated at one time in the rotating drum, with about 900 liters of emulsified mixture. This mixing procedure is a step taken to promote better quality consistency on the coating of Lano-E composite 2. The treated glove 1 will then be dried through a series of carefully controlled drying procedures in a tumbling dryer. The tumbling mechanism is preferred because the system ensures each and every piece of the gloves 1 is kept in continuous motion while they are being dried. Such drying process is conducive for the formation of a thin and uniform coating of the Lano-E composite 2 on the glove 1. The coating may vary, with a preferred range of from about 0.005 millimeters to about 0.02 millimeters.

The drying process may vary in length of time and temperature. In one effective variation the water or other liquid carrying medium of the composite is slowly evaporated in two stages:

| Parameters for First Drying (D1) | | |
|---|---|---|
| Stage | Drying Temperature (° C.) | Drying Time(minute) |
| 1 | 40 to 50 | 20 |
| 2 | 50 to 60 | 50 to 60 |

| Parameters for Second Drying (D2) | | |
|---|---|---|
| Stage | Drying Temperature (° C.) | Drying Time(minute) |
| 1 | 50 to 60 | 50 to 60 |

Upon completion of the first drying process (D1), the glove 1 is inverted again so that the glove 1 returns to its normal orientation where the donning surface 4 faces inside. The gloves 1 are subsequently subjected to the Second Drying (D2) process until complete dryness is achieved.

Excessive heating can bring about quality problems in which the glove 1 may turn brownish in color and develop a pungent smell on completion of the drying process.

Besides the built-in automated temperature regulating system, each drying machine is installed with an over-heating alarm system as an additional quality control feature to safeguard the quality of the drying process. Should the drying temperature exceed the required setting, a warning signal will be triggered and the heating mechanism will be deactivated immediately. The faulty unit will not be used until it is repaired.

The gloves 1 are inverted in between the First Drying (D1) and the Second Drying (D2). This glove 1 inversion is so that the glove 1 returns to its normal orientation, where the donning surface 4 faces inside and is the internal portion of the glove. The inversion processes are performed manually with the aid of air nozzles driven by vortex blowers.

At the completion of the process the donning surface 4 is uniformly coated with a layer of dehydrated Lano-E composite 2, which is comprised of measured parts of Lanolin and Vitamin E that is adequate to provide a well balanced, nongreasy optimum smoothness for the wearer of the glove 1.

Several factors in the process contribute to the ultimate satisfactory coating of dehydrated Lano-E composite 2, including, but not limited to, the ratio of Lanolin and Vitamin-E, the quantity of Lanolin and Vitamin-E applied to the donning surface 4, the chlorine wash, the component ratios in the emulsified mixture with the water, and the staged drying process.

Although the present invention has been described in considerable detail with regard to the preferred versions thereof, other versions are possible. Therefore, the appended claims should not be limited to the descriptions of the preferred versions contained herein.

What is claimed is:

1. A method of manufacturing a hand health care disposable glove comprising:
   a) forming a disposable glove from natural rubber latex or other synthetic materials selected from the group consisting of acrylonitrile, polyurethane, polychloroprene or polyvinyl chloride through a dipping process, wherein in normal orientation the glove having an interior with a donning surface and having an exterior surface;
   b) inverting said glove inside out, whereby the donning surface is exposed;
   c) subjecting said glove through a chlorination washing process;
   d) covering the donning surface of said glove with a coating of an emulsified mixture of Lanolin and Vitamin E (Lano-E composite) using a liquid medium, wherein the Lano-E composite comprises by weight of about 5 parts of pure Lanolin, about 15 parts of Vitamin E, and, about 80 parts of the liquid medium, wherein the Lano-E composite is formed by blending Lanolin and Vitamin E homogeneously with water between about 35 degrees Celsius and about 55 degrees in Celsius, wherein the glove is agitated in the emulsified mixture for about 5 minutes;
   e) evaporating the liquid medium from the emulsified mixture in a heating condition, whereby a dried coating of the Lano-E composite is formed on the donning surface of said glove, wherein evaporating comprises a first stage for about 20 minutes at 40 to 50 degrees in Celsius and a second stage for about 50 to 60 minutes at 50 to 60 degrees Celsius;
   f) inverting said glove such that the donning surface is taken inside; and
   g) drying the glove in a single stage for 50 to 60 minutes at 50 to 60 degrees in Celsius.

2. The method of claim 1, wherein the liquid medium comprises water.

3. The method of claim 1, wherein said comprises purified lanolin enriched with Vitamin E.

4. The method of claim 3, wherein said covering comprises soaking said glove into said emulsified mixtures of Lanolin and Vitamin E in said liquid medium.

5. The method of claim 3, wherein said covering comprises spraying said medium.

6. The method of claim 1, further comprising pre-treating the donning surface of said glove with a series of two or more chlorination washing processes prior to covering the donning surface with said emulsified mixture of Lanolin and Vitamin E using said liquid medium.

7. The method of claim 1, wherein the Vitamin E is in the form of alpha-tocopheryl acetate.

8. The method of claim 1, wherein the Lano-E composite is formed by blending Lanolin and Vitamin E homogeneously with about 45 degrees Celsius water.

9. The method of claim 1, wherein a thickness of the coating of the Lano-E composite when dehydrated is between about 0.005 mm and about 0.02 mm.

10. The method of claim 9, wherein a thickness of the coating of the Lano-E composite when dehydrated is about 0.01 mm.

11. The method of claim 1, further comprising a first rinsing of the glove, prior to the inversion of said glove, whereby the rinsing removes powder residue.

12. The method of claim 11, further comprising a second rinsing of the glove, following the inversion of said glove, whereby the rinsing removes powder residue.

13. The method of claim 12, further comprising a third rinsing of the glove, following the chlorination washing process, whereby the rinsing removes chlorination residue.

14. The method of claim 13, above further comprising a fourth rinsing of the glove, following the chlorination washing process, whereby the rinsing removes chlorination residue.

* * * * *